United States Patent [19]

Woods

[11] Patent Number: 5,180,366
[45] Date of Patent: Jan. 19, 1993

[54] APPARATUS AND METHOD FOR ANGIOPLASTY AND FOR PREVENTING RE-STENOSIS

[76] Inventor: W. T. Woods, R.R. 1-Box 13, Chatham, Ill. 62629

[21] Appl. No.: 597,483

[22] Filed: Oct. 10, 1990

[51] Int. Cl.⁵ .............................................. A61M 25/10
[52] U.S. Cl. ........................................ 604/96; 606/194
[58] Field of Search ............................. 604/96–103; 606/191, 192, 194

[56] References Cited

U.S. PATENT DOCUMENTS

| | | | |
|---|---|---|---|
| 4,423,725 | 1/1984 | Baran et al. | 604/101 |
| 4,693,243 | 9/1987 | Buras | 604/101 |
| 4,994,033 | 2/1991 | Shockey et al. | 604/96 |

FOREIGN PATENT DOCUMENTS 8912478  12/1989  World Int. Prop. O. .......... 604/104

*Primary Examiner*—C. Fred Rosenbaum
*Assistant Examiner*—William Lewis
*Attorney, Agent, or Firm*—Hill, Van Santen, Steadman & Simpson

[57] ABSTRACT

The present invention provides an angioplasty method and apparatus for performing same that reduces or eliminates restenosis in arteries that have undergone angioplasty. The invention prevents the proliferative response. To this end, the present invention provides a method and apparatus for depositing a time release anti-proliferation agent in the artery wall. The anti-proliferation agents inhibit the proliferation of cells that cause re-stenosis.

24 Claims, 1 Drawing Sheet

APPARATUS AND METHOD FOR ANGIOPLASTY AND FOR PREVENTING RE-STENOSIS

BACKGROUND OF THE INVENTION

The present invention relates to the treatment of cardiovascular disease. More specifically, the present invention relates to an apparatus and method for angioplasty that prevents re-stenosis.

Cardiovascular disease is the leading cause of death in the United States. Arteriosclerosis refers generally to a group of diseases in which the lumen of an artery becomes narrowed or blocked (occluded). The narrowing of the artery restricts blood flow to the organ that is nourished by the artery. The reduced blood flow results in the deterioration of the organ to the point wherein the organ can be permanently damaged unless the blockage of blood flow is removed.

When an artery that serves the heart is narrowed or blocked, this pathological process results in a heart attack. A variety of therapies have been developed to prevent heart attacks and to restore adequate blood flow to the heart. These therapies include dilating the artery utilizing a pharmaceutical, surgical intervention by replacing the blocked segment with a new segment (or coronary artery by-pass graft), or the use of a catheter-mounted mechanical device, such as a balloon.

Although in most cases, surgery is required to reestablish an occluded lumen to proper diameter, by-pass surgery and the like presents a number of disadvantages to the patient. By-pass surgery is quite expensive, creates a period of discomfort for the patient, and involves the surgical risks associated with any major surgery. Therefore, the focus recently has been on relatively noninvasive and less risky alternatives to conventional surgery.

One such method is known as angioplasty, or when used with coronary arteries, percutaneous transluminal coronary angioplasty. Generally, angioplasty is performed using a multilumen inflatable balloon catheter. At least one lumen of the catheter is open ended and allows the passage of a guide wire, or in some instances, the direct intra-arterial infusion of a pharmaceutical agent therethrough. In angioplasty, the guide wire is directed to the area of arterial narrowing using x-ray monitoring, for example, a roentgengraph or fluoroscope. Thereafter, the catheter is positioned with the aid of the guide wire in the region of arterial narrowing.

Concentric with the lumen that includes the guide wire is a second lumen that is connected to an elongated inflatable segment or balloon portion. This balloon portion is located near the distal end of the catheter and is constructed from a material having a high tensile strength and low elasticity. The second lumen and balloon are generally filled with diluted contrast medium. The contrast medium is a radiopaque liquid that makes the visualization of the catheter possible by fluoroscopy.

The typical angioplasty procedure involves the introduction of the catheter into the arterial system of the patient, for example, through the femoral artery of the leg. The catheter is then guided to the affected artery, for example, the left anterior descending coronary artery, manually with the aid of fluoroscopy.

Once the catheter is appropriately positioned in the affected artery, the guide wire is advanced to and past the point of obstruction. The balloon portion of the catheter, which surrounds the guide wire, is thereby advanced along the guide wire until it is in juxtaposition to the occluded segment. The balloon is then inflated. As the balloon expands, it pushes the occluding tissue toward the walls of the vessel. This correspondingly increases the diameter of the occluded artery.

Typically, the balloon is inflated and deflated a number of times. By repeatedly inflating and deflating the balloon, it is hoped that the corresponding repeated deformation of the occluding tissue will permanently deform the tissue thus providing the affected artery with a lumen having a sufficiently large inner diameter.

After the balloon has been inflated and deflated an arbitrary number of times, the balloon is then collapsed and retracted. The site of obstruction is then examined angiographically. This is often performed by injecting a radiopaque dye through the lumen housing the guide wire. If the artery is still occluded, the procedure is repeated.

Examples of such catheters include Medtronic Thruflex and Advanced Cardiovascular Systems catheters.

The popularity of angioplasties has increased dramatically. In the United States in 1989, hundreds of thousands of angioplasties were performed. This number is rapidly increasing. Fortunately, for many patients, angioplasty permanently reopens the previously occluded arteries. However, in 30% of the occluded arteries which are opened by an angioplasty technique, the arteries re-occlude within six months of the procedure. This results in symptoms of cardiac ischemia, such as chest pain, exercise intolerance, and shortness of breath. The patient's risk of disabling or fatal heart attack is markedly increased.

It is believed that re-stenosis in a previously treated segment of an artery is due to the stretch-induced damage of arterial tissue. The response to the damage caused by the inflation of the balloon catheter is an exaggerated healing response that includes proliferation of the undamaged tissue. The proliferating tissues are the endothelial cells that form the lining of the lumen and fibroblasts and smooth muscle cells that reside in the artery wall.

In attempting to prevent re-stenosis from occurring, vascular stents have been installed within the artery for the purpose of holding the lumen open. However, this has been found to be an unsatisfactory solution since proliferating tissue will grow around and through the stent lattice re-occluding the lumen. Accordingly, there is a need for preventing or reducing restenosis in arteries that have undergone angioplasty.

SUMMARY OF THE INVENTION

The present invention provides an angioplasty method and apparatus for performing same that reduces or eliminates restenosis in arteries that have undergone the angioplasty. The invention prevents the proliferative response. Pursuant to the present invention, growth and division of endothelial cells is promoted selectively, while inhibiting proliferation of other cells, such as fibroblasts and smooth muscle cells. Further, pursuant to the present invention, the endothelial cell lining of the lumen becomes complete (confluent) and proliferation of all other cell types is inhibited.

To this end, the present invention provides a method and apparatus for depositing a time release anti-proliferation agent in the artery wall. The anti-proliferation agents inhibit the proliferation of cells that cause re-stenosis.

In an embodiment, a multilumen catheter is provided having a distal end including an inflatable balloon and means for implanting an anti-proliferation agent in a lining of a vessel wall located in juxtaposition to the balloon.

In an embodiment, the anti-proliferation agent is at least one agent chosen from the group consisting of: antibiotics; anti-metabolites; cytotoxic agents; steroids; hormones; antiparasitics; anti-platelet; anticoagulants; calcium channel blockers; anti-hyperlipemics; alpha receptor blockers; beta receptor blockers; anti-connective tissue agents; anti-smooth muscle agents; and endothelial growth stimulators.

In an embodiment, a multilumen catheter for performing angioplasty and limiting or preventing re-stenosis is provided comprising a shaft defining a first lumen. An inflatable balloon is located at an end of the shaft. A drug delivery collar including a plurality of perforations for receiving at least one anti-proliferative agent is located in juxtaposition to said balloon. And the catheter includes means for embedding the anti-proliferation agents in the collar in tissue in a vessel.

In an embodiment, the collar includes a plurality of perforations or chambers for receiving the anti-proliferative agent and is so constructed and arranged that upon the application of a sufficient pressure through the catheter the anti-proliferative agents are expelled from the perforations.

The present invention also provides a method for increasing the diameter of an occluded vessel comprising the steps of: inserting a catheter having an inflatable balloon and means for implanting anti-proliferative agents into a predetermined vessel; positioning the means for implanting in juxtaposition to the occluded portion of the vessel; implanting an anti-proliferation agent into the lining of the occluded portion of the vessel; locating the balloon in juxtaposition to the occluded portion of the vessel; and inflating and deflating the balloon at least once to increase the diameter of the occluded vessel.

In an embodiment of the method, suction is applied by the catheter within th vessel prior to the implantation step to pull tissue of the vessel near the means for implanting.

In an embodiment of the method, the anti-proliferation agent is implanted by pulsing a pressure through the catheter.

In an embodiment of the method, after the anti-proliferation agent is implanted, the balloon catheter is inflated to further embed the agent in the tissue.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention provides an apparatus and method for removing arterial occlusions and eliminating or limiting re-stenosis. Although angioplasty is a procedure of choice for reopening occluded blood vessels, due to its relative safety, a major draw back is that approximately 30% of the treated vessels reocclude within six months. The re-stenosis usually results due to an over proliferation of cells in the treated areas. Pursuant to the device and method of the present invention, occluded arteries are opened and time releasable drugs are implanted in the artery walls. The implanted drugs inhibit cell proliferation that causes re-stenosis.

Figure 1:
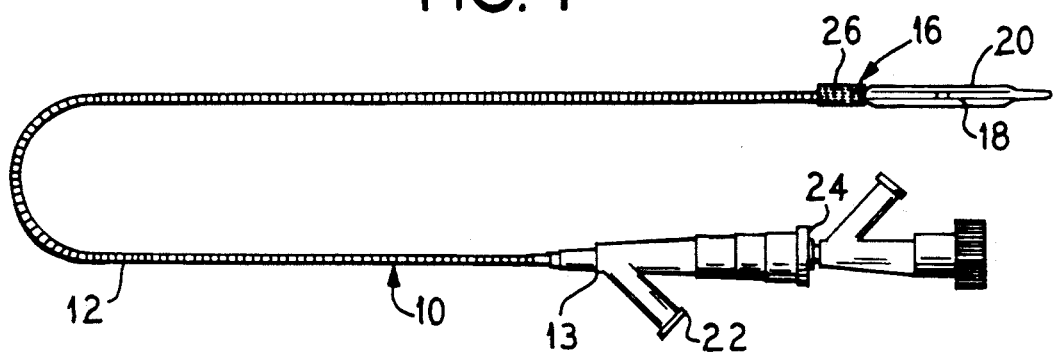
FIG. 1 illustrates a perspective view of an embodiment of the catheter of the present invention.

Referring now to FIG. 1, a multi-lumen catheter 10 is illustrated. The catheter 10 of the present invention includes a first shaft or lumen 12 that extends from a first end 13 of the catheter to a distal end 16 of the catheter. The lumen 12 is preferably surrounded by a steel spring coil having a polyethylene outer jacket.

Located within the first lumen 12 is a second lumen or guide wire 18. As is known in the art, the guide wire 18 functions to guide the catheter 10 to the desired location within a vessel 19.

Located preferably at the distal end 16 of the catheter 10 and secured to the first shaft 12 is an inflatable member such as a balloon lumen 20. The balloon lumen 20 preferably is constructed from a material having a high tensile strength and low elasticity. For example, the balloon lumen 20 can be constructed from an inflatable polyethylene material.

Located at the first end 13 of the catheter 10 are two ports 22 and 24. The first port 24 functions to receive the guide wire 18 and the second port 22 provides a means for inflating the balloon portion 20 of the catheter when the catheter 10 is in proper position. In these regards, the catheter 10 generally is similar to catheters such as Medtronic Model 18K-20-25E catheter.

Figure 2:
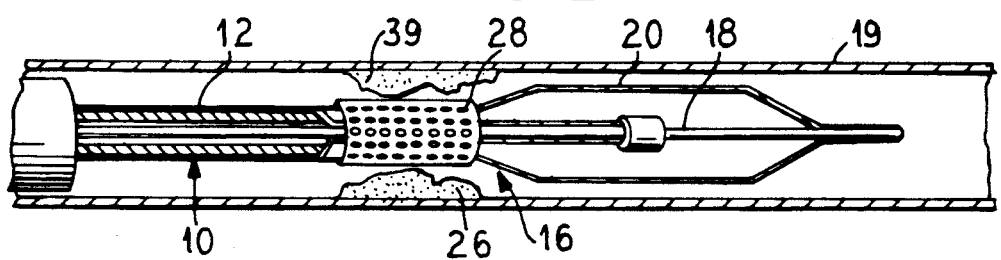
FIG. 2 illustrates a cross-sectional enlarged view of a portion of the catheter in an occluded artery.
Figure 3:
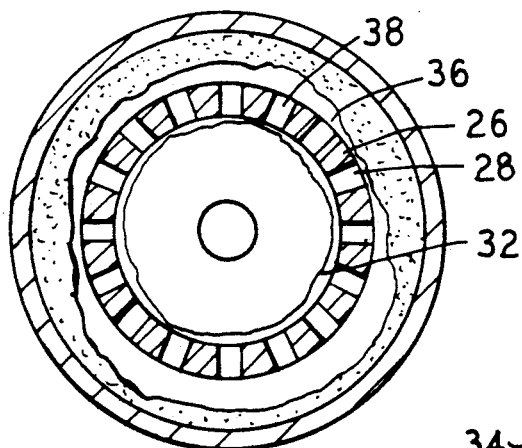
FIG. 3 illustrates a cross-sectional view of the catheter of FIG. 2 taken along lines III—III of FIG. 2.

In contrast to a standard catheter, however, the present invention provides a catheter that includes means for delivering an anti-proliferation agent to select tissue in the vessel. The anti-proliferation agent prevents re-stenosis by preventing cell proliferation after the angioplasty. In the preferred embodiment illustrated, the means for delivering an anti-proliferation agent is a drug delivery collar 26. As illustrated in FIG. 2, the drug delivery collar 26 is located around the distal end 16 of the catheter 10 and a portion of the balloon lumen 20.

The drug delivery collar 26 includes a plurality of perforations (holes) or chambers 28. Each of the perforations 28 is filled with an anti-proliferation agent, preferably drug delivery pellets. For example, theoretically, for a 0.4 millimeter in diameter (a in FIG. 4) ×0.4 millimeter deep (b in FIG. 4) hole, approximately $50 \times 10^3$ (50,000) drug pellets having a 10 micron diameter can be housed therein.

Figure 4:
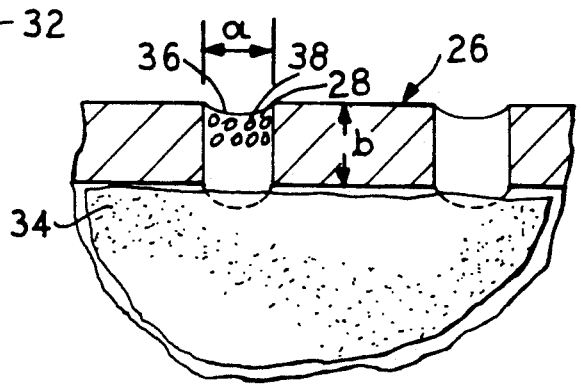
FIG. 4 illustrates a detailed cross-sectional view of a perforation in the collar of the catheter of FIG. 2.

Referring now to FIG. 4, a cross-sectional view of a perforation 28 and the drug delivery collar 26 is illustrated. The drug delivery collar 26 preferably is constructed from a stainless steel tube having a plurality of perforations 28. The inner surface 32 of the drug delivery collar 26 includes a flexible floor or lining 34. The perforations 28 terminate in an opening 36 in fluid communication with the outside environment.

The flexible lining 34 of the drug delivery collar 26 is so constructed and arranged so that it will allow the pellets 38 contained within the chambers 28 to be expelled therefrom upon a pulse of a sufficient pressure through the interior defined by the collar. It has been found that a layer of polyethylene approximately 30 microns thick functions satisfactorily in this regard. The polyethylene can be applied on the interior 32 of the collar 26 as a liquid and then dries as a film.

To fill the collar 26, the collar can be submerged in the applicable drug delivery pellets containing the anti-proliferation agent. The collar 26 is then agitated causing the pellets 38 to be received within the perforations 28 of the collar. Excess pellets 28 that adhere to the collar 26 outside the perforations can be removed by brushing the collar.

As stated above, the drugs that are located within the perforations are drugs that inhibit the cell proliferation that causes re-stenosis. Examples of such anti-proliferation agents include: antibiotics (e.g., adriamycin, Adria); anti-metabolites (e.g., methotrexate, Lederle); cytotoxic agents (e.g., cytoxan, Bristol-Myers); steroids (e.g., celestrone, Schering); hormones (e.g., estrogen, Upjohn); antiparasitics (e.g., chloroquine, Winthrop); anti-platelet (e.g., salicylates, SmithKline); anticoagulants (e.g., heparin, Wyeth-Ayerst); calcium channel blockers (e.g., cardizem, Marion Merrell Dow); anti-hyperlipemics (e.g., mevacor, Merck), alpha receptor blockers (e.g., hytrin, Abbott); beta receptor blockers (e.g., sectral, Wyeth-Ayerst); anti-connective tissue agents (e.g., neuraminidase, Sigma); antismooth muscle agents (e.g., cicletanide, Sigma); and endothelial growth stimulators (e.g., endothelial growth factor, Genentech). A preferred agent for use in the present invention is chloroquine (e.g., Aralen by Winthrop). Of course, the agents can be used in combination.

Preferably, the pellets 38 are constructed of a polymeric material such as polyethylene or metallic beads coated with a polymeric material. The polymeric material forms a matrix that includes the agent. Examples of such polymeric material are available from Promeon, Inc. (Minneapolis). The polymeric material is designed to release the drug or agent at a steady rate, for example six months. Each pellet can be coated with a laminin (Cooper Biomedical), a naturally occurring protein that adheres to living tissue surfaces.

By way of example, and not limitation, an example of the catheter of the present invention is as follows.

The balloon lumen 20 shaft's outside diameter is 0.038 inches concentric to a 0.035 inch outside diameter lumen and is coated with silicon (0.018 inch diameter). The overall catheter 10 length is approximately 56 inches. The outside diameter is 0.038 inch (3.5 French) except the final 0.75 inch tip which has an 0.031 inch outside diameter. The inside diameter of the tip is 0.020 inches. The balloon's 20 length is 30 millimeters, the diameter is 2.5 millimeters when inflated to a pressure of 5 atmospheres.

The collar 26 is located so that it covers approximately 10 millimeters of the length of the balloon 20. In this regard, the collar is approximately 10 millimeters in length and made of 0.4 millimeter thick stainless steel or other rigid material perforated by approximately 100, 0.4 millimeter diameter, chambers 28 having a depth of 0.4 millimeters. The collar has an outside diameter of 3.0 millimeters and an inside diameter of 2.2 millimeters. The collar's 26 inner surface 32 is lined with a layer 34 of polyethylene 30 millimeters thick which forms the floor of each perforation 28 in the collar 26.

The catheter 10 is advanced through the vessel 19 so that the collar 26 is positioned so that it is surrounded by the atheroma 39 as illustrated in FIG. 2. The balloon 20 is then inflated to two atmospheres pressure to occlude the distal artery lumen and press the inner lining 32 of the collar 26 firmly against the floor 34 of each pellet containing chamber or perforation 28.

A negative 1.0 atmosphere pressure is applied to the lumen of the guide catheter 10. This creates a negative pressure within the narrow region and pulls the arterial tissue 39 into contact with the drug delivery collar 26.

A square wave pressure pulse of 20 atmospheres is then delivered for 100 milliseconds to the balloon 20. The pressure is delivered through a port 22 that communicates with a pulse generator (not illustrated). Examples of pulse generators that can be utilized are piston driven devices available from Medical Engineering Consultants or compressed gas devices available from, for example, Daisy Corporation.

The pulse within the balloon 20 drives the flexible lining 32 of the pellet containing perforations 28 outward propelling the pellets 38 toward the narrowed arterial tissue 39. The pellets 38 adhere to and embed within the artery tissue 39 and drugs begin to elute from them. The balloon 20 is deflated.

The catheter 10 is then positioned so that the balloon 20 is located in the narrowed arterial region. The balloon 20 is inflated again to a pressure of 5 atmospheres or more to dilate the narrow region and to promote adhesion between the pellets and arterial tissue 39. After two minutes or so, and multiple inflations of the balloon, or other appropriate time determined by the physician, the balloon 20 is deflated and the pellet implanting balloon catheter is retracted into the guide catheter which is then removed from the patient.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

I claim:

1. An apparatus for performing angioplasty comprising:
   a multilumen catheter having an inflatable balloon and a separate means for implanting an anti-proliferation agent that is in the form of a pellet in a lining of a vessel wall, the means for implanting being located in juxtaposition to the balloon, the means for implanting including a rigid collar including a plurality of apertures for receiving the pellet and including means for expelling the pellet from the collar without increasing the exterior circumferences of the collar.

2. The apparatus of claim 1 wherein the antiproliferation agent includes at least one agent chosen form the group consisting of: antibiotics; anti-metabolites; cytotoxic agents; steroids; hormones; antiparasitics; antiplatelets; anticoagulants; calcium channel blockers; anti-hyperlipemics; alpha receptor blockers; beta receptor blockers; anti-connective tissue agents; anti-smooth muscle agents; and endothelial growth stimulators.

3. The apparatus of claim 1 wherein the catheter includes a guide wire located at least partially within a first lumen for guiding the catheter to a desired location within the vessel.

4. The apparatus of claim 1 wherein the inflatable balloon is located at a distal end of the catheter.

5. The apparatus of claim 1 wherein the means for implanting includes means for removably receiving the antiproliferation agent.

6. A multilumen catheter for performing angioplasty comprising:
   an inflatable balloon located at a distal end of the catheter;
   a rigid nonexpandable collar for implanting an anti-proliferation agent, the agent being in the form of pellets in a lining of a vessel wall, the collar including apertures for receiving the pellets; and
   means for expelling the pellets from the apertures without expanding the outer circumference of the collar.

7. The multilumen catheter of claim 6 wherein the anti-proliferation agent is at least one agent chosen from the group consisting of: antibiotics; anti-metabolites; cyctotoxic agents; steroids; hormones; antiparasitics; anti-platelets; anticoagulants; calcium channel blockers; anti-hyperlipemics; alpha receptor blockers; beta receptor blockers; anti-connective tissue agents; anti-smooth muscle agents; and endothelial growth stimulators.

8. The multilumen catheter of claim 6 wherein the collar includes a plurality of holes for receiving the antiproliferation agent.

9. The multilumen catheter of claim 6 wherein the collar includes a flexible lining.

10. The multilumen catheter of claim 9 wherein the flexible lining is constructed from polyethylene.

11. The multilumen catheter of claim 6 wherein the collar includes a plurality of perforations for receiving the anti-proliferation agent and is so constructed and arranged that upon the application of a sufficient pressure through the catheter the anti-proliferation agents are expelled from the perforations.

12. The multilumen catheter for performing angioplasty and limiting or preventing re-stenosis comprising:
   a shaft defining a first lumen;
   an inflatable balloon located at an end of the shaft;
   a rigid drug delivery collar including a plurality of chambers for receiving at least one anti-proliferation agent, the agent being in the form of pellets, the collar being located in juxtaposition to said balloon; and
   means for expelling the anti-proliferation agents from the collar without expanding an outer circumference of the collar, and embedding the agent in tissue in a vessel.

13. The multilumen catheter of claim 12 wherein the anti-proliferation agent is at least one agent chosen from the group consisting of: antibiotics; anti-metabolites; cytotoxic agents; steroids; hormones; antiparasitics; anti-platelets; anticoagulants; calcium channel blockers; anti-hyperlipemics; alpha receptor blockers; beta receptor blockers; anti-connective tissue agents; anti-smooth muscle agents; and endothelial growth stimulators.

14. The multilumen catheter of claim 12 wherein the collar includes a flexible lining.

15. The multilumen catheter of claim 12 wherein the collar is so constructed and arranged that upon the application of a sufficient pressure through the catheter the anti-proliferation agents are expelled from the chambers.

16. The multilumen catheter of claim 12 wherein the means for embedding includes means for generating a pulse of pressure upon a floor of the collar that defines a bottom of the chamber.

17. The multilumen catheter for performing angioplasty and limiting or preventing re-stenosis comprising:
   a shaft defining a first lumen;
   an inflatable balloon located at an end of the shaft;
   a drug delivery collar including a plurality of chambers for receiving at least one anti-proliferation agent, the collar being located in juxtaposition to said balloon; and
   means for embedding the anti-proliferation agents int he collar in tissue in a vessel, the means for embedding includes a pulse generators.

18. A method for increasing ht diameter of an occluded vessel comprising the steps of:
   inserting a catheter having a first section including an inflatable balloon and a second section including means for implanting anti-proliferation agents into a predetermined vessel;
   positioning the means for implanting in juxtaposition to an occluded portion of the vessel;
   implanting an anti-proliferation agent into a lining of the occluded portion of the vessel;
   moving the catheter to locate the first section including the inflatable balloon in juxtaposition to the occluded portion of the vessel; and
   inflating and deflating the balloon at least once to increase the diameter of the occluded vessel.

19. The method of claim 18 wherein the anti-proliferation agent is at least one agent chosen from the group consisting of: antibiotics; anti-metabolites; cytotoxic agents; steroids; hormones; antiparasitics; anti-platelets; anticoagulants; calcium channel blockers; anti-hyperlipemics; alpha receptor blockers; beta receptor blockers; anti-connective tissue agents; anti-smooth muscle agents; and endothelial growth stimulators.

20. A method for increasing the diameter of an occluded vessel comprising the steps of:
   inserting a catheter having an inflatable balloon and means for implanting anti-proliferation agents into a predetermined vessel;
   positioning the means for implanting in juxtaposition to an occluded portion of the vessel, after the means for implanting are in juxtaposition to the occluded portion of the vessel, suction is applied by the catheter to pull tissue of the vessel near the means for implanting;
   implanting an anti-proliferation agent into a lining of the occluded portion of the vessel;
   locating the balloon in juxtaposition to the occluded portion of the vessel; and
   inflating and deflating the balloon at least once to increase the diameter of the occluded vessel.

21. The method of claim 18 wherein the anti-proliferative agent is implanted by pulsing a pressure through the catheter.

22. The method of claim 18 wherein the anti-proliferative agent is implanted, the balloon catheter is inflated to further embed the agent in the tissue.

23. A method for limiting or preventing re-stenosis in a patient in need of same comprising providing an anti-proliferation agent int he form of pellets, implanting, using a catheter having a rigid portion that receives and expels pellets, in an occluded portion of a vessel the pellets, and increasing the diameter of the occluded portion using a second expandable portion of the catheter.

24. The method of claim 23 wherein the anti-proliferation agent is at least one agent chosen from the group consisting of: antibiotics; anti-metabolites; cytotoxic agents; steroids; hormones; antiparasitics; anti-platelets; anticoagulants; calcium channel blockers; anti-hyperlipemics; alpha receptor blockers; beta receptor blockers; anti-connective tissue agents; anti-smooth muscle agents; and endothelial growth stimulators.

* * * * *